United States Patent [19]

Chaiet

[11] 4,172,940
[45] Oct. 30, 1979

[54] PURIFICATION OF C-076 COMPOUNDS BY SINGLE COLUMN CHROMATOGRAPHY

[75] Inventor: Louis Chaiet, Springfield, N.J.

[73] Assignee: Merck & Co., Inc., Rahway, N.J.

[21] Appl. No.: 838,693

[22] Filed: Oct. 3, 1977

[51] Int. Cl.$^2$ ............................................. C07H 17/08
[52] U.S. Cl. ................................................. 536/17 A
[58] Field of Search ....................... 260/343.41; 536/17

[56] References Cited

U.S. PATENT DOCUMENTS 3,950,360  4/1976  Aoki et al. ....................... 260/343.41

OTHER PUBLICATIONS

Mishima et al. Tetrahedrun Letters 10, pp. 711–714, 1975.
Jour. of Antibiotics 29(6), Jun. 1976, pp. 76–35 to 76–42 and pp. 76–14 to 76–16.
Derwent Abstracts 76268w/46 to Sankyo Co.
Snyder et al. Introduction to Modern Liquid Chromatography, John Wiley & Sons.

*Primary Examiner*—Alan L. Rotman
*Assistant Examiner*—Jane T. Fan
*Attorney, Agent, or Firm*—David L. Rose; Richard A. Thompson; Harry E. Westlake

[57] ABSTRACT

This case relates to a novel process for aiding in the isolation and purification of novel compounds which are produced by the microorganism, *Streptomyces avermitilis*. The process described herein utilizes a bed of activated alumina and a bed of activated carbon, respectively. The compounds which are isolated and purified are described generically as C-076 and have significant parasiticidal activity.

1 Claim, No Drawings

PURIFICATION OF C-076 COMPOUNDS BY SINGLE COLUMN CHROMATOGRAPHY

SUMMARY OF THE INVENTION

This invention is directed to a process for isolating the novel chemical compounds C-076 which are produced by the fermentation of a nutrient medium with a strain of the microorganism, Streptomyces avermitilis.

The compounds, to which the novel techniques of isolation and purification of this invention are directed, are described in co-pending U.S. application Ser. No. 772,601 of G. Albers-Schonberg, R. Burg, T. Miller, R. Ormond and H. Wallich. Said application teaches the use and characterization of the C-076 compounds as well as the utilization and characterization of the microorganism, Streptomyces avermitilis. Said application is hereby incorporated by reference in this application.

The microorganisms capable of producing these C-076 compounds are of a new species of the genus Streptomyces, which has been named Streptomyces avermitilis. One such culture, isolated from soil is designated MA-4680 in the culture collection of Merck & Co., Inc., Rahway, N.J. A C-076 producing sample of this culture has been deposited in the permanent culture collection of the Fermentation Section of the Northern Utilization Research Branch, U.S. Department of Agriculture at Peoria, Ill., and has been assigned the accession number NRRL 8165. A sample of NRRL 8165 has also been deposited, without restriction as to availability, in the permanent culture collection of the American Type Culture Collection at 12301 Parklawn Drive, Rockville, Md. 20852, and has been assigned the accession number ATCC 31,267. The microbiological culture Streptomyces avermitilis also embraces mutants of the said microorganism. For example, those C-076 producing mutants which are obtained by natural selection or those produced by mutating agents including X-ray irradiation, ultraviolet irradiation, nitrogen mustard or like treatments are also included within the ambit of this invention.

One example of such an organism is a strain of Streptomyces avermitilis MA 4848 which was isolated after irradiation with ultraviolet light of Streptomyces avermitilis MA 4680. A lyophilized tube and a frozen vial of this culture has been deposited in the permanent culture collection of the American Type Culture Collection, and they have been assigned the accession numbers 31272 and 31271 respectively. Slightly higher fermentation yields of C-076 have been obtained using this frozen stock as inoculum.

The C-076 compounds are believed to have the following planar structural formula:

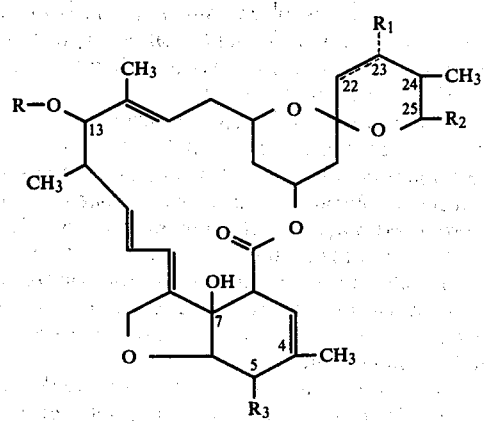

wherein R is the α-L-oleandrosyl-α-L-oleandroside of the structure:

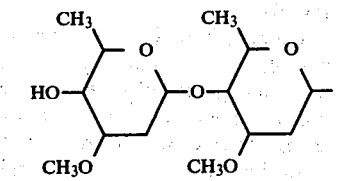

and wherein
the broken line indicates a single or a double bond;
$R_1$ is hydroxy and is present only when said broken line indicates a single bond.
$R_2$ is propyl or butyl; and
$R_3$ is methoxy or hydroxy.

In the foregoing structural formula, the individual compounds are as set forth below.

| | $R_1$ | $R_2$ | $R_3$ |
|---|---|---|---|
| A1a | Double bond | butyl | —OCH$_3$ |
| A1b | Double bond | propyl | —OCH$_3$ |
| A2a | —OH | butyl | —OCH$_3$ |
| A2b | —OH | propyl | —OCH$_3$ |
| B1a | Double bond | butyl | —OH |
| B1b | Double bond | propyl | —OH |
| B2a | —OH | butyl | —OH |
| B2b | —OH | propyl | —OH |

More particularly, this invention is comprised of a novel technique wherein it is an object of this process to aid in the isolation of the parasiticidal active compound in a substantially purified form. Further objects of this invention will become apparent from the following description.

DESCRIPTION OF THE INVENTION

In accordance with this invention, novel techniques of extraction and fractionation are utilized to isolate and purify substances generically described herein as C-076. These substances are prepared by growing under controlled conditions strains of microorganisms of Streptomyces avermitilis. These substances are described as C-076 A1a, A1b, A2a, A2b, B1a, B1b, B2a and B2b.

In particular, this invention is directed to removing impurities from C-076 non-polar solvent solutions wherein said solvent solution is passed through a single column containing a bed of activated alumina and a bed of activated carbon, respectively followed by elution with said solution solvent containing a polar solvent.

Some of the non-polar solvents that can be utilized in the instant invention are methylene chloride, chloroform, benzene, hexane and the like.

Some polar solvents that can be utilized in the elution solution are isopropanol, isobutanol and the like.

The amount of polar solvent that can be utilized with the non-polar solvent can range from about 1–10%. A more preferred range of polar solvent is about 3%.

A method of utilizing the activated alumina and activated carbon is to place the alumina as the bottom layer in a column and the carbon as the top layer. The activated alumina can be a commercially available acid washed activated alumina.

The C-076 compounds are produced during the aerobic fermentation of suitable aqueous nutrient media under conditions described hereinafter, with a producing strain of *Streptomyces avermitilis*. Aqueous media such as those used for the production of many antibiotic substances are suitable for use in this process for the preparation of C-076.

Such nutrient media contain sources of carbon and nitrogen assimilable by the microorganism and generally low levels of inorganic salts. In addition, the fermentation media may contain traces of metals necessary for the growth of the microorganisms. These are usually present in sufficient concentration in the complex sources of carbon and nitrogen which may be used as nutrient sources, but can, of course, be added separately to the medium if desired.

In general, carbohydrates such as sugars, for example dextrose, sucrose, maltose, lactose, dextran, cerelose and the like, and starches are suitable sources of assimilable carbon in the nutrient media. The exact quantity of the carbon source which is utilized in the medium will depend, in part, upon the other ingredients in the medium but it is usually found that an amount of carbohydrate between about 0.5 and 5% by weight of the medium is satisfactory. These carbon sources can be used individually or several such carbon sources may be combined in the same medium.

Various nitrogen sources such as yeast hydrolysates, yeast autolysate, soybean meal, casein hydrolysates, yeast extracts, corn steep liquors, distillers solubles, cottonseed meal, meat extract and the like, are readily assimilable by *Streptomyces avermitilis* in the production of the C-076 compounds. The various sources of nitrogen can be used alone or in combination in amounts ranging from about 0.2 to 6% by weight of the medium.

Among the nutrient inorganic salts which can be incorporated in the culture media are the customary salts capable of yielding sodium, potassium, magnesium, ammonium, calcium, phosphate, sulfate, chloride, carbonate and like ions. Also included are trace metals such as cobalt, manganese, iron and the like.

The fermentation employing the C-076-producing microorganisms can be conducted at temperatures ranging from about 20° C. to about 40° C. For optimum results, it is most convenient to conduct these fermentations at a temperature in the range of from about 24° C. to about 30° C. Temperatures of about 27° C.–28° C. are most preferred. The pH of the nutrient medium suitable for producing the C-076 compounds can vary from about 5.0 to 9.0 with a preferred range of from about 6.0 to 7.5.

Small scale fermentations are conveniently carried out by placing suitable quantities of nutrient medium in a flask employing known sterile techniques, inoculating the flask with either spores or vegetative cellular growth of a C-076-producing strain of *Streptomyces avermitilis*, loosely stoppering the necks of the flask with cotton, and permitting the fermentation to proceed in a constant room temperature of about 28° C. on a rotary shaker for about 3 to 10 days. For larger scale work, it is preferable to conduct the fermentation in suitable tanks provided with an agitator and a means of aerating the fermentation medium. The nutrient medium is made up in the tank and after sterilization is inoculated with a suitable source of vegetative cellular growth of a C-076 producing strain of *Streptomyces avermitilis*. The fermentation is allowed to continue for from 1 to 8 days while agitating and/or aerating the nutrient medium at a temperature in the range of from about 24° C. to 37° C. The degree of aeration is dependent upon several factors such as the size of the fermentor, agitation speed and the like. Generally, the larger scale fermentations are agitated at about 95 to 150 rpm and about 2 to 20 cubic feet per minute of air.

The substances of this invention, which are generically referred to herein as C-076, are found primarily in the mycelium on termination of the *Streptomyces avermitilis* fermentation, and may be recovered and separated from one another as described below. Four major and four minor components of the C-076 as elaborated by *Streptomyces avermitilis* have been isolated. The eight different compounds are identified herein as C-076 A1a, A1b, A2a, A2b, B1a, B1b, B2a and B2b.

The major C-076 compounds are not produced in equal amounts by the fermentations described herein. In general, it has been found that the A1 compounds comprise about 20 to 30% by weight of the total C-076 complex produced, the A2 compounds about 1 to 20% and the B1 and B2 compounds each about 25 to 35%.

The separation of the C-076 series of compounds from the whole fermentation broth and the recovery of the individual components is carried out by solvent extraction and application of chromatographic fractionations with various chromatographic techniques and solvent systems.

The C-076 compounds have slight solubility in water, but are soluble in organic solvents. This property may be conveniently employed to recover them from the fermentation broth. Thus in one recovery method, the whole fermentation broth is filtered and the aqueous filtrate discarded. The wet mycelial cake is then extracted with an appropriate organic solvent. While any organic solvent may be employed, it is preferable to use a water miscible solvent such as acetone, methanol, ethanol and the like. Generally, several extractions are desirable to achieve maximum recovery. The solvent removes the C-076 active components as well as other substances lacking the anti-parasitic activity of C-076. Since other substances may be on the solvent solution containing the C-076, it becomes necessary or desirable to remove the undesirable substances.

In later techniques to separate the C-076 components as mentioned above, other more expensive techniques and expensive solid supports are utilized. Thus, it becomes important to remove as many impurities and color agents from the C-076 solution before component separation.

This invention utilizes a novel technique for removing undesirable color and impurities from a C-076 non-polar solvent solution by passing it through a single column bed containing both activated alumina and activated carbon, respectively.

The following examples are capable of wide variation and modification, and any minor departure or extension is considered as being within the skill of the artisan and as falling within the scope of this invention.

EXAMPLE 1

A 250-ml. baffled Erlenmeyer flask containing 50 ml. of the following medium:

| Lactose | 2.0% |
|---|---|
| Distiller's Solubles | 1.5% |
| Autolyzed yeast, Ardamine pH | 0.5% |
| pH--before sterilization | 7.0 | is inoculated with the contents of one frozen vial of *Streptomyces avermitilis* MA-4848 and incubated on a rotary shaker at 28° C. for 24 hours at 150 rpm.

Ten ml. of the above fermentation media is employed to inoculate 500 ml. of the same medium as above in a 2-liter baffled Erlenmeyer flask. The fermentation media is incubuated at 150 rpm on a rotary shaker at 28° C. for 24 hours.

All of the foregoing media is employed to inoculate 467 liters of the following media in a 756-liter stainless steel fermentor:

| Lactose | 2.0% |
|---|---|
| Distiller's Solubles | 1.5% |
| Autolyzed yeast, Ardamine pH | 0.5% |
| Polyglycol 2000 | 0.32 ml./liter |
| pH--before sterilization | 7.0 |

The fermentation media is incubated at 28° C. for 40 hours with an air flow 10 cubic feet per minute and an agitation rate of 130 rpm.

230 Liters of the above media is employed to inoculate 4,310 liters of the following medium in a 5,670-liter stainless steel fermentor:

| Dextrose | 4.5% |
|---|---|
| Peptonized Milk | 2.4% |
| Autolyzed yeast, Ardamine pH | 0.25% |
| Polyglycol 2000 | 2.5 ml./liter |
| pH--before sterilization | 7.0 |

The fermentation continues for 144 hours at 26° C. with an air flow rate of 54.3 cubic feet per minute and agitation rate of 120 rpm.

The fermentation media are filtered and the mycelial filter cake washed with about 550 liters of water, the filtrate and washings are discarded. The filter cake is agitated with about 1500 liters of acetone for about one hour and filtered. The filter cake is washed with a mixture of about 150 liters of acetone and 40 liters of deionized water affording about 2000 liters of extract.

The foregoing fermentation and extraction is repeated on the same scale affording a further 200 liters of acetone extract which is combined with the first extract and evaporated to a volume of about 800 liters. The pH of the concentrate is adjusted to about 4.7 with concentrated hydrochloric acid and combined with about 800 liters of methylene chloride. The combined solvents are agitated for about 4 hours and separated. The aqueous layer is combined with an additional 800 liters of methylene chloride and agitated for about 4 hours. The layers are separated and each methylene chloride extract separately treated with about 10 kilograms of Super-Cel and filtered. Both extracts are evaporated to a combined volume of about 60 liters.

EXAMPLE 2

The 60-liter solution of C-076 in methylene chloride of the previous example is concentrated to dryness in vacuo and the residue is combined three times with 60 liter portions of methanol and evaporated to dryness to remove any residual methylene chloride. The final methanol concentrate volume is approximately 36 liters. The methanol solution is stored overnight and filtered. The filter cake is washed with 40 liters of fresh methanol and the methanol filtrates and washings are combined. The methanol solution is combined with 95 liters of ethylene glycol and 130 liters of heptane. The 2-layer solution is agitated for 5 minutes and the lower layer (ethylene glycol and methanol) is separated. The heptane solution is washed with a mixture of 20 liters of ethylene glycol and 6.3 liters of methanol. After 5 minutes of agitation, the lower layer is separated and combined with the first ethylene glycol/methanol extract. An equal volume of water (approximately 150 liters) containing 79 g. of salt per liter is added to the ethylene glycol/methanol extracts. This solution is extracted with 150 liters of ethyl ether with agitation for 5 minutes. The ether layer is washed with 75 liters of water (½ volume) and agitated for 5 minutes and the layers separated. This procedure is repeated an additional 2 times (the final water wash contains 20 g. of salt per liter) affording a final ether layer volume of 110 liters. The ether layer is concentrated in vacuo, to a minimum volume, keeping the temperature less than 25° C. Forty liters of methylene chloride is added to the residue and the solution is evaporated to dryness. This procedure is repeated and the final residue concentrated in vacuo at 50° C. to dryness.

EXAMPLE 3

A 30-centimeter diameter column is prepared with a layer of 34 kilograms of activated alumina followed by a layer of 34 kilograms of activated carbon in a solution of methylene chloride. The residue from the previous example (3410 g. of solids containing 1565 g. of C-076 product) is dissolved in methylene chloride to a volume of 34 liters and applied to the column and eluted with 34 liters of methylene chloride. These fractions are discarded. A 3% solution of isopropanol and methylene chloride (20.8 liters of isopropanol and 660 liters of methylene chloride) is applied to the column and eluted in approximately 200-liter fractions. The most active combined isopropanol and methylene chloride fractions containing 2290 g. of solids and 1312 g. of C-076 product are evaporated in vacuo at a bath temperature of about 60° C. to a volume of about 20 liters. The bath temperature is reduced to about 45° C. and the extract is evaporated to dryness in vacuo. The residue is dissolved in 10 parts methylene chloride, 10 parts hexane and one part methanol to a final volume of 15 liters.

EXAMPLE 4

A column is prepared containing 750 g. of MERCK acid washed alumina in methylene chloride and 400 g.

of Pittsburgh CAL type granular carbon (12-40 mesh) on top of the alumina in the same solvent.

Twenty-nine hundred ml. of 8714-65G, a methylene chloride solution of chemotherapeutic agent C-076 is put through the column at a rate of 125 ml. per minute followed successively by: 2 liters of $CH_2Cl_2$, 2 liters each of 1% isopropanol-$CH_2Cl_2$, 2% isopropanol-$CH_2Cl_2$, 3% isopropanol-$CH_2Cl_2$ and 4% isopropanol-$CH_2Cl_2$. One liter effluent fraction is taken and evaluated by the dried solids content and C-076 assay. The results are as follows:

| Fraction | Volume | Total Solids | C-076 Content | C-076 Purity | C-076 Yield |
|---|---|---|---|---|---|
| Feed | 2900 ml. | 205 g. | 34.0 g. | 16.5% | |
| Fractions 3-8 | 6000 ml. | 98 g. | 30.9 g. | 31.5% | 91% |
| Fractions 9-12 | 4000 ml. | 13 g. | 5.8 g. | 44.6% | 17% |

What is claimed is:

1. A method for removing impurities from C-076 non-polar solvent solutions in which said C-076 compounds have the formula:

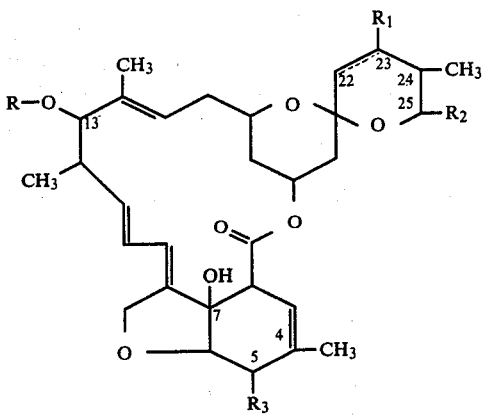

wherein R is the α-L-oleandrosyl-α-L-oleandroside of the structure:

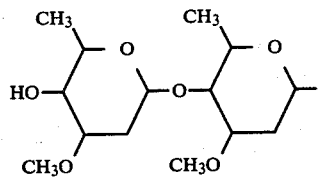

and wherein
the broken line indicates a single or a double bond;
$R_1$ is hydroxy and is present only when said broken line indicates a single bond
$R_2$ is propyl or butyl; and
$R_3$ is methoxy or hydroxy,
wherein said solvent solution is passed through a single column containing both a bed of acid washed activated alumina and a bed of activated carbon, respectfully followed by elution with a non polar solvent selected from methylene chloride, chloroform, benzene or hexane containing from about 1-10% of isopropanol.

* * * * *